United States Patent [19]

Moore

[11] 4,357,345

[45] Nov. 2, 1982

[54] SUBSTITUTED FURANS

[75] Inventor: George G. I. Moore, Houlton, Wis.

[73] Assignee: Riker Laboratories, Inc., Northridge, Calif.

[21] Appl. No.: 324,064

[22] Filed: Nov. 23, 1981

[51] Int. Cl.³ .................... A61K 31/34; C07D 307/42
[52] U.S. Cl. .................................. 424/285; 549/497; 549/501
[58] Field of Search ...................... 260/347.8; 424/285

[56] References Cited

U.S. PATENT DOCUMENTS

| 4,124,725 | 11/1978 | Moore | 424/330 |
| 4,128,664 | 12/1978 | Moore | 424/324 |
| 4,172,082 | 10/1979 | Moore | 549/72 |
| 4,172,151 | 10/1979 | Moore | 424/330 |
| 4,222,883 | 9/1980 | Clinton | 260/347.8 X |

OTHER PUBLICATIONS

White and Glossman, *Prostaglandins*, 7, 123, (1974).
Adamkiewicz et al., *Canad. J. Biochem. Physiol.*, 33:332, (1955).
Selye, *Brit. Med. J.*, 2:1129, (1949).
Winter, *Proc. Exper. Biol. Med.*, 111:544, (1962).

*Primary Examiner*—Richard Raymond
*Attorney, Agent, or Firm*—Cruzan Alexander; Donald M. Sell; David R. Cleveland

[57] ABSTRACT

3,5-di(t-butyl)-4-hydroxyphenyl- and 3,5-di(t-butyl)-4-hydroxybenzoyl-substituted furans have pharmacological activity as antiinflammatory agents.

15 Claims, No Drawings

SUBSTITUTED FURANS

TECHNICAL FIELD

This invention relates to certain substituted furan compounds, to the use of such compounds as anti-inflammatory agents, and to novel intermediates useful for preparing final product compounds of the invention.

Background Art

I have previously synthesized and described several antiinflammatory compounds containing di(t-butyl)-phenol groups. Information regarding these compounds is contained in U.S. Pat. Nos. 4,128,664 (2,6-di(t-butyl)-phenol substituted in the 4-position by an N-substituted carboxamido group), 4,124,725 (2,6-di(t-butyl)phenol substituted in the 4-position by an optionally substituted benzoyl group), 4,172,151 (2,6-di(t-butyl)phenol substituted in the 4-position by an optionally substituted phenyl group), and 4,172,082 (2,6-di(t-butyl)phenol substituted in the 4-position with optionally substituted thiophenyl groups).

Disclosure of Invention

The above described compounds are antiinflammatory agents useful in the treatment of inflammation related conditions such as rheumatoid arthritis. Many of the above compounds also have activity as stabilizers against oxidation, and this characteristic may be related to the efficacy of the above compounds as antiinflammatory agents, although there is no present confirmation of this possibility. The 3,5-di(t-butyl)-4-hydroxyphenyl moiety found in each of the above compounds is also found in the well-known antioxidant 3,5-di(t-butyl)-4-hydroxytoluene (commonly referred to as butylated hydroxytoluene, or "BHT"), a substance which is frequently used as a food additive to extend the shelf life of processed foods. BHT itself has little or no pharmacological value as an antiinflammatory agent. Likewise, many other compounds containing groups derived from di(t-butyl)phenol have little or no pharmacological value, e.g., 2,6-di(t-butyl)-phenol, 4-carboxamido-2,6-di(t-butyl)phenol, 4-(2-chlorobenzoyl)-2,6-di(t-butyl)phenol, 4-(5-carboxy-2-thenoyl)-2,6-di(t-butyl)phenol, 2,6-di(t-butyl)-4-phenylsulfonylphenol, 4-acetyl-2,6-di(t-butyl)phenol, and 4-n-octyl-2,6-di(t-butyl)phenol.

Compounds other than those already described in the above-mentioned patents containing 3,5-di(t-butyl)-4-hydroxyphenyl groups may also have pharmacological activity as antiinflammatory agents. However, at the present time there appear to be no rules by which one could correlate structural similarities between various compounds containing the 3,5-di(t-butyl)-4-hydroxyphenyl moiety with the presence of useful antiinflammatory activity in such compounds. New antiinflammatory compounds containing the 3,5-di(t-butyl)-4-hydroxyphenyl moiety must be discovered by trial and error synthesis and testing.

The present invention provides, in one aspect, compounds of the formula:

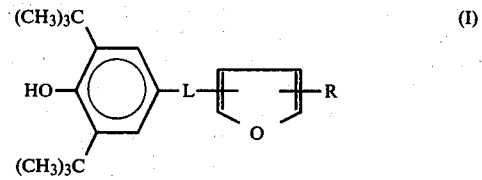

wherein L is a carbon-carbon bond between the benzene ring and the 2-position of the furan ring, or a carbonyl radical bonded to any available position of the furan ring, and R is hydrogen, chloro, bromo, iodo, or methyl. These compounds have useful antiinflammatory activity. The present invention also provides antiinflammatory compositions containing such compounds, methods for combatting inflammatory reactions in mammals, and novel intermediates useful in preparing such compounds.

DETAILED DESCRIPTION

In the practice of the present invention, compounds wherein L is a carbon-carbon bond are prepared by the reaction of 2,6-di(t-butyl)benzoquinone with an organometallic reagent such as a magnesium reagent or a lithium reagent prepared from an appropriate halogenated or alkylated furan (Process A). Halogenated and alkylated furans are known to the art, as are procedures for their preparation. Among the known halogenated and alkylated furans are 2-iodofuran, 2-bromofuran, 2-chlorofuran, 2-bromo-5-chlorofuran, 2,5-dibromofuran, 2-methylfuran and the like.

Such reactions between the magnesium or lithium reagents of furans and 2,6-di(t-butyl)benzoquinones provide the intermediate optionally substituted 2,6-bis(t-butyl)-4-hydroxy-4-furyl-2,5-cyclohexadien-1-ones having the formula:

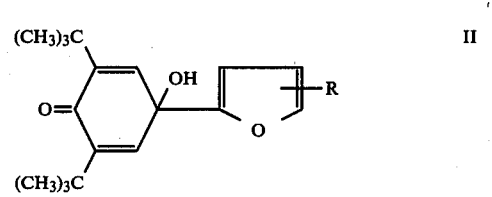

wherein R is as defined above for Formula I. These compounds (Formula II) are novel and fall within the scope of the present invention. They are reduced to form compounds of Formula I, using hydrogen gas with a catalyst such as palladium on charcoal or Raney nickel, or by using a metal hydride reducing agent such as lithium aluminum hydride, or by using hydrogen iodide.

The compounds of the invention wherein L is a carbonyl radical are prepared by several methods. The reaction of 3,5-di(t-butyl)-4-hydroxybenzoyl chloride with optionally substituted furans in the presence of Friedel-Crafts catalysts (Process B) is useful for the synthesis of compounds wherein L is a carbonyl radical bonded to the 2-position of furan and R is in the 5-position. Friedel-Crafts catalysts which are useful include aluminum chloride, titanium tetrachloride, zinc chloride and the like. Such reactions are generally carried out by dissolving the benzoyl chloride compound in an inert solvent such as carbon disulfide, dichloroethane, dichloromethane and the like, optionally under an inert gas atmosphere such as nitrogen, adding the Friedel- Crafts catalyst at room temperature, adding the furan compound dropwise, and allowing the reaction to progress to completion (as shown by completion of hydrogen chloride evolution). Heating or warming can sometimes be useful to promote the reaction.

Alternatively 2,6-di(t-butyl)phenol can be reacted in the Friedel-Crafts reaction with an appropriate furancarbonyl chloride (Process C.) The procedure is essentially as above, using standard Friedel-Crafts techniques. A weaker catalyst such as titanium tetrachloride is preferred if the reaction rate is too rapid with aluminum chloride. Another alternative is direct introduction of one or two tertiary butyl groups into the 4'-furylphenol or 4'-furoylphenol nucleus by a Friedel-Crafts reaction.

Another method for the snythesis of compounds of the invention wherein L is a carbonyl radical is reaction of the novel Grignard compound 3,5-di(t-butyl)-4-trimethylsilyloxy)phenylmagnesium bromide with an optionally substituted cyanofuran such as 5-chloro-2-cyanofuran, 5-bromo-2-cyanofuran, 3-methyl-2-cyanofuran, 5-methyl-2-cyanofuran and the like (Process D). These intermediates are known or are readily prepared from the corresponding known carboxylic acids by known methods.

Preferably, L is a carbonyl radical. Particularly preferred compounds of the invention are 2,6-di(t-butyl)-4-(2'-furoyl)phenol, 2,6-di(t-butyl)-4-(3'-furoyl)phenol, 2,6-di(t-butyl)-4-(5'-methyl-2'-furoyl)-phenol, and 2,6-di(t-butyl)-4-(3'-methyl-2'-furoyl)phenol, and the preparation of these compounds is described below in Examples 1, 2, 5, and 6, respectively.

In addition to their use as effective anti-inflammatory agents, the compounds of the invention are relatively active as stabilizers to prevent oxidation. Some also are analgesics, some are antipyretic agents, and some have mild immunosuppressant activity.

In order to determine and assess pharmacological activity, testing in animals is carried out using various assays known to those skilled in the art. Thus, the antiinflammatory activity of compounds of the invention can be conveniently demonstrated using an assay designed to measure the ability of these compounds to inhibit the enzyme prostaglandin synthetase (cyclooxygenase), such as the test described in White and Glossman, *Prostaglandins*, 7, 123 (1974). The antiinflammatory activity of the compounds of the invention can also be demonstrated using an assay designed to test the ability of these compounds to antagonize the local edema which is characteristic of the inflammatory response (the rat food edema test). The compounds of the invention are also active when administered dermally. Such topical activity has been measured by means of the guinea pig erythema test and by a contact sensitivity test. Antiflammatory activity can also be detected by other assays known to the art such as the cotton pellet granuloma test and the adjuvant arthritis test. Analgesic activity has been observed using standard test methods such as the phenylquinone writhing (mouse) and Randall-Selitto (rat) tests.

Leading references to the rat food edema method are:
(1) Adamkiewicz et al, *Canad. J. Biochem. Physiol.*, 33:332 (1955);
(2) Selye, *Brit. Med. J.*, 2:1129 (1949); and
(3) Winter, *Proc. Exper. Biol. Med.*, 111:544 (1962).

The edema test is performed on adult female rats. Generally, one group of 10 rats serves as non-medicated controls, while another group of 10 rats receives the test compound at various times prior to the induction of the edema, usually 15 minutes, one hour and/or 18 hours. The test compound is administered orally as a suspension in a 4 percent aqueous solution of acacia. Edema is induced by the plantar injection of 0.5 percent carrageenin (0.1 ml/foot) into the right hind foot. The left hind foot receives a like volume of 0.9 percent saline solution. Three hours later, the volume of each hind foot is determined plethysmographically. The edema is expressed as the increase in the volume of the edemogen injected foot less the volume of the saline injected foot. The percent inhibition is calculated by dividing the mean increase in the edema of the medicated group by the mean increase in the edema of the non-medicated group, subtracting this quotient from 1, and multiplying the resulting number by 100. An active dose is that giving a statistically significant inhibition of the induced edema, usually in the range of at least about 25–35 percent inhibition. The preferred compounds of the invention shown in Examples 1, 2, 5, and 6 below exhibit 54 percent, 48 percent, 48 percent, and 39 percent inhibition, respectively, in the above test at doses of 100 mg/kg.

The compounds of the invention preferably are administered orally but other known methods of administration can also be used, e.g., dermatomucosally (for example dermally, rectally and the like), parenterally (for example by subcutaneous injection, intramuscular injection, intraarticular injection, intravenous injection and the like), and by ocular administration. Effective dosages should be less than a toxic amount. Such dosages ordinarily fall within the range of about 1 to 500 mg of the compound of the invention per kg of body weight of the mammal to be treated. Oral dosages are usually below 100 mg/kg. The compounds of the invention ordinarily are administered in the form of compositions containing the compound together with a pharmaceutically acceptable carrier. Suitable compositions for oral administration are in the form of liquids (such as 4 percent acacia and polyethylene glycol solutions), tablets (which can contain anhydrous lactose, microcrystalline cellulose, modified starch, calcium stearate and talc, as well as other conventional compounding agents together with the active antiinflammatory agents), solid suspensions and capsules. Pharmaceutically acceptable carriers for topical application include creams, gels, tapes and the like. Liquid formulations, such as solutions or suspensions of the active ingredient in inert carriers, can be used for dosage by injection.

Using the methods described above, the preparation of compounds of the invention is illustrated in the following examples. The purpose of the examples is to enable those skilled in the art to practice the invention, and they are not intended to limit in any way the scope of the invention.

EXAMPLE 1

Preparation of a Compound wherein L is Carbonyl, Using Process B

To a stirred solution of 40.3 g (0.15 mole) of 3,5-di(t-butyl)-4-hydroxybenzoyl chloride in 400 ml of dichloroethane was added slowly 28.6 g of titanium tetrachloride. After ten minutes, 10.3 g (0.15 mole) of furan was added dropwise. The mixture was stirred under a nitrogen atmosphere for about sixteen hours, then poured carefully into 10% hydrochloric acid. The solution was extracted with dichloromethane, and the extracts washed with 10% hydrochloric acid and dried over magnesium sulfate. Evaporation provided a residue which was recrystallized from a benzene-hexane mixture after treating with decolorizing charcoal. The solid obtained was sublimed at 130° to 137° C. at 0.04 mm Hg to provide white solid 2,6-di(t-butyl)-4-(2'-furoyl)-phenol, m.p. 148°–149° C.

| Analysis: | % C | % H |
| --- | --- | --- |
| Calculated for $C_{19}H_{24}O_3$: | 76.0; | 8.0 |
| Found: | 76.3; | 8.2. |

EXAMPLE 2

Preparation of a Compound wherein L is Carbonyl, Using Process C

Step 1

A solution of 20 g (0.18 mole) of furan-3-carboxylic acid in 75 ml of dichloromethane, 100 ml of thionyl chloride, and a few drops of N,N-dimethylformamide was heated at its reflux temperature for about sixteen hours. An additional 20 ml of thionyl chloride was added, and refluxing then continued for 8 more hours. The mixture was evaporated to provide a residue which was distilled at 38° to 42° C. at 0.4 mm Hg. The furan-3-carboxylic acid chloride structure of the product was confirmed by infrared spectral analysis.

Step 2

To a solution of 15.1 g (0.116 mole) of furan-3-carboxylic acid chloride in 100 ml of dichloroethane under a nitrogen atmosphere was added slowly 15.6 g (0.128 mole) of aluminum chloride. After stirring 10 minutes, a solution of 23.8 g (0.116 mole) of 2,6-di(t-butyl)phenol in dichloroethane was slowly added. The mixture was heated to 70° C. for 30 minutes, then poured carefully into 10% hydrochloric acid. The mixture was extracted with dichloromethane and the extracts washed with 10% hydrochloric acid, then dried over magnesium sulfate. Evaporation provided a residue which was crystallized by cooling in petroleum ether, then recrystallized from hexane with treatment with decolorizing charcoal. The product was 2,6-di(t-butyl)-4-(3'-furoyl)-phenol, in the form of off-white flakes, m.p. 141.5°–144° C.

| Analysis: | % C | % H |
| --- | --- | --- |
| Calculated for $C_{19}H_{24}O_3$: | 76.0; | 8.0 |
| Found: | 76.2; | 8.0. |

EXAMPLE 3

Preparation of a Compound wherein L is a Carbon-Carbon Bond, Using Process A

Step 1

A stirred solution of 27.0 g (0.184 mole) of 2-bromofuran in 200 ml of diethyl ether under a nitrogen atmosphere was chilled to about −70° C. and 0.184 mole of n-butyl lithium in hexane was then added to the stirred solution. To this solution was added 40.5 g (0.184 mole) of 2,6-di(t-butyl)benzoquinone while maintaining the temperature at −70° C. The solution was allowed to warm slowly to about 25° C., then 100 ml of five percent hydrochloric acid was added with stirring. The ether solution was dried over magnesium sulfate, filtered, then evaporated to provide a residue which was washed thoroughly with hexane to provide white solid 2,6-di(t-butyl)-4-hydroxy-4-(2'-furyl)-2,5-cyclohexadien-1-one. The structure was confirmed by infrared and nuclear magnetic resonance spectral analysis.

Step 2

To a stirred solution of 15 g (0.052 mole) of 2,6-di(t-butyl)-4-hydroxy-4-(2'-furyl)-2,5-cyclohexadien-1-one in 250 ml of diethyl ether was added excess lithium aluminum hydride. Stirring was continued for 30 minutes after completion of the exotherm. The resulting mixture was treated carefully with a mixture of ethanol, water and 10% hydrochloric acid to effect hydrolysis. The ether layer was separated and dried. Evaporation provided a residue which was suspended in a small amount of petroleum ether and chilled at −20° C. for about sixteen hours. The solid product was separated by filtration and purified by sublimation at 90° to 105° C. at about 0.4 mm Hg. The sublimed solid was recrystallized from hexane to provide very pale yellow crystals of 2,6-di(t-butyl)-4-(2'-furyl)phenol, m.p. 103.5°–105.5° C.

| Analysis: | % C | % H |
| --- | --- | --- |
| Calculated for $C_{18}H_{24}O_2$: | 79.4; | 8.9 |
| Found: | 79.6; | 9.0. |

EXAMPLE 4

Preparation of a Compound Wherein L is Carbonyl, Using Process D

To a mixture of 54.06 g (0.371 mole) of 5-chlorofuran-2-carboxamide and 66 g of pyridine was added slowly, with stirring, 65.5 g (0.371 mole) of benzenesulfonyl chloride. The resulting mixture was then heated to 75° C. and maintained between 75° and 80° C. for 15 minutes. After cooling to ambient temperature, the reaction was quenched by pouring the reaction mixture into an equal volume of water. Dilute hydrochloric acid was added to the quenched reaction mixture to adjust the pH to 7 to 8. Salt water and ethyl acetate were added, and the organic phase then separated and dried over magnesium sulfate. The dried organic phase was evaporated to provide an oil which was distilled at 65° C. under about 8 mm Hg to provide 5-chloro-2-cyanofuran.

A Grignard reagent was prepared by reacting 0.1 mole of 3,5-di(t-butyl)-4-trimethylsilyloxybromobenzene with magnesium turnings in dry tetrahydrofuran. The mixture was heated at reflux and 12.7 g (0.1 mole) of 5-chloro-2-cyanofuran was added slowly thereto. The resulting mixture was maintained at reflux for about 16 hours and then cooled. To the cooled reaction mixture was added 150 ml of ten percent hydrochloric acid, followed by heating of the reaction mixture at reflux for 6 hours. After cooling, a tetrahydrofuran layer was separated. The water layer was extracted with dichloromethane, and the organic extracts were combined with the tetrahydrofuran and dried over anhydrous magnesium sulfate. The solution was filtered, then evaporated to provide an oil. The oil was fractionated by high pressure liquid chromatography on a silica gel column, eluting with 2:1 hexane:dichloromethane. The product was obtained as a solid and recrystallized from hexane to give tan plates of 2,6-di(t-butyl)-4-(5'-chloro-2'-furoyl)phenol, m.p. 116.5°–118.5° C.

| Analysis: | % C | % H |
|---|---|---|
| Calculated for C₁₉H₂₃ClO₃: | 68.1 | 6.9 |
| Found: | 68.1 | 7.0 |

EXAMPLE 5

Preparation of a Compound Wherein L is Carbonyl, Using Process D

To a mixture of 44 g (0.123 mole) of 3,5-di(t-butyl)-4-trimethylsilyloxybromobenzene in 200 ml of tetrahydrofuran was added 0.15 mole of magnesium turnings in a small quantity of tetrahydrofuran. A few drops of dibromoethane were added to the above mixture. The resulting mixture was heated to reflux, then refluxed for three hours. This solution was added to a stirred refluxing solution of 13.1 g (0.123 mole) of 2-cyano-5-methylfuran in 100 ml of tetrahydrofuran. After refluxing for three hours and cooling, an excess of ten percent hydrochloric acid was added. The mixture was extracted with dichloromethane, the extracts washed with water, and the organic layer dried over magnesium sulfate. The organic layer was evaporated to provide a solid which was stirred with hot hexane, treated with decolorizing charcoal, filtered and cooled. The solid obtained was recrystallized three times from hexane to provide tan plates of 2,6-di(t-butyl)-4-(5'-methyl-2'-furoyl)phenol, m.p. 115.5°–117° C.

| Analysis: | % C | % H |
|---|---|---|
| Calculated for C₂₀H₂₆O₃: | 76.4 | 8.3 |
| Found: | 76.4 | 8.4 |

EXAMPLE 6

Preparation of a Compound Wherein L is Carbonyl, Using Process D

To a stirred flask containing excess concentrated ammonium hydroxide was added gradually 50 g of 3-methyl-2-furoyl chloride. The resulting mixture was extracted with dichloromethane. The extracts were dried, then evaporated to provide solid 3-methylfuran-2-carboxamide.

To a solution of 29 g (0.231 mole) of 3-methylfuran-2-carboxamide in 42 g of pyridine was added dropwise with stirring 41 g (0.23 mole) of benzenesulfonyl chloride. The mixture was maintained below 60° C. by external cooling. After formation of a solid, water was added to the mixture. The aqueous mixture was extracted with 300 ml of diethyl ether. The ether layer was dried over magnesium sulfate, then evaporated. The product was distilled at 90°–95° C. at a pressure of 5–10 mm Hg to provide 2-cyano-3-methylfuran as a colorless liquid.

Using the method of Example 5, 10.7 g (0.10 mole) of 2-cyano-3-methylfuran was reacted with the Grignard reagent of 3,5-di(t-butyl)-4-trimethylsilyloxybromobenzene to provide white crystals of 2,6-di(t-butyl)-4-(3'-methyl-2'-furoyl)phenol, m.p. 115°–116° C. after recrystallization from hexane.

| Analysis: | % C | % H |
|---|---|---|
| Calculated for C₂₀H₂₆O₃: | 76.4 | 8.3 |
| Found: | 76.4 | 8.5 |

EXAMPLE 7

Preparation of a Compound Wherein L is Carbonyl, Using Process B

Using the method of Example 1, 2-iodofuran could be reacted to provide 2,6-di(t-butyl)-4-(5'-iodo-2'-furoyl)phenol.

EXAMPLE 8

Preparation of a Compound Wherein L is Carbonyl, Using Process B

Using the method of Example 1, 2-bromofuran could be reacted to provide 2,6-di(t-butyl)-4-(5'-bromo-2'-furoyl)phenol.

EXAMPLE 9

Preparation of a Compound Wherein L is a Carbon-Carbon Bond, Using Process A

Using the method of Example 3, 2-bromo-3-chlorofuran could be reacted to provide the intermediate compound 2,6-di(t-butyl)-4-hydroxy-4-(3'-chloro-2'-furyl)-2,5-cyclohexadien-1-one. This intermediate then could be reacted as in Example 3 to provide 2,6-di(t-butyl)-4-(3'-chloro-2'-furyl)phenol.

Various modifications and alterations of this invention will be apparent to those skilled in the art without departing from the scope and spirit of this invention and the latter should not be restricted to that set forth herein for illustrative purposes.

What is claimed is:

1. Compounds of the formula:

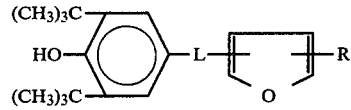

wherein L is a carbon-carbon bond between the benzene ring and the 2-position of the furan ring, or a carbonyl radical bonded to any available position of the furan ring, and R is hydrogen, chloro, bromo, iodo, or methyl.

2. Compounds according to claim 1, wherein L is a carbonyl radical.

3. Compounds according to claim 1, wherein L is a carbon-carbon bond.

4. Compounds according to claim 1, wherein R is hydrogen.

5. Compounds according to claim 1, wherein R is chloro.

6. Compounds according to claim 1, wherein R is bromo.

7. Compounds according to claim 1, wherein R is iodo.

8. Compounds according to claim 1, wherein R is methyl.

9. The compound 2,6-di(t-butyl)-4-(2'-furoyl)phenol according to claim 1.

10. The compound 2,6-di(t-butyl)-4-(3'-furoyl)phenol according to claim 1.

11. The compound 2,6-di(t-butyl)-4-(5'-methyl-2'-furoyl)phenol according to claim 1.

12. The compound 2,6-di(t-butyl)-4-(3'-methyl-2'-furoyl)phenol according to claim 1.

13. Antiinflammatory compositions, comprising at least one compound according to claim 1 together with a pharmaceutically acceptable carrier.

14. A method for combatting inflammatory reactions in a mammal which comprises administering to said mammal an effective dose, less than a toxic amount, of one or more compositions according to claim 13.

15. A method according to claim 14, wherein said composition is administered orally.